(12) United States Patent
Kato (10) Patent No.: US 10,596,040 B2
(45) Date of Patent: Mar. 24, 2020

(54) TRANSDERMAL ADMINISTRATION DEVICE (71) Applicant: TOPPAN PRINTING CO., LTD., Taito-ku (JP)

(72) Inventor: Hiroyuki Kato, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 7 days.

(21) Appl. No.: 15/659,733

(22) Filed: Jul. 26, 2017

(65) Prior Publication Data
US 2017/0319393 A1 Nov. 9, 2017

Related U.S. Application Data (63) Continuation of application No. PCT/JP2016/050847, filed on Jan. 13, 2016.

(30) Foreign Application Priority Data

Jan. 27, 2015 (JP) .................. 2015-013559

(51) Int. Cl.
*A61F 13/02* (2006.01)
*A61M 37/00* (2006.01)

(52) U.S. Cl.
CPC .......... *A61F 13/02* (2013.01); *A61M 37/0015* (2013.01); *A61M 2037/0023* (2013.01); *A61M 2037/0046* (2013.01)

(58) Field of Classification Search
CPC ....... A61K 9/703; A61F 13/02; A61F 13/024; A61F 13/0236; A61F 13/0226;
(Continued)

(56) References Cited

U.S. PATENT DOCUMENTS 5,533,962 A * 7/1996 Peterman ............ A61F 13/0203
602/41
2008/0274166 A1* 11/2008 Sacks ..................... A61K 9/703
424/449
(Continued)

FOREIGN PATENT DOCUMENTS

JP  1990-68824 U   5/1990
JP  1992-97811 U   8/1992
(Continued)

OTHER PUBLICATIONS

International Search Report dated Mar. 22, 2016 in PCT/JP2016/050847, filed Jan. 13, 2016.

*Primary Examiner* — Bhisma Mehta
*Assistant Examiner* — Nidah M Hussain
(74) *Attorney, Agent, or Firm* — Oblon, McClelland, Maier & Neustadt, L.L.P.

(57) ABSTRACT

A transdermal administration device including an administration member including a substrate having first and second surfaces, and a projection protruding from the first surface, a first adhesive sheet adhered to and extending outward from the second surface, a second adhesive sheet adhered to and extending outward from the first adhesive sheet, and a cover including a main body and a flange extending outward from an edge of the main body. The main body and the flange form a structure body including a remaining portion which includes at least a portion of the flange and is configured to remain on the second adhesive sheet, a tear-off portion which includes at least a portion of the main body and is configured to be separated from the remaining portion, and a tear-off assistance portion configured to facilitate formation of a cut for separating the tear-off portion from the remaining portion.

20 Claims, 4 Drawing Sheets

(58) Field of Classification Search
CPC .. A61F 13/0259; A61F 13/60; A61F 13/0008; A61F 13/0246; A61F 15/005; A61F 15/004; A61F 2013/008; A61M 2025/0246; A61M 2037/0023; A61M 2037/0007; A61M 37/0015; A61B 2050/316
USPC ......................................................... 604/173
See application file for complete search history.

(56) References Cited

U.S. PATENT DOCUMENTS

| | | | |
|---|---|---|---|
| 2010/0256568 A1* | 10/2010 | Frederickson | A61M 37/0015 604/173 |
| 2012/0029434 A1* | 2/2012 | Kobayashi | A61M 37/0015 604/173 |
| 2015/0335870 A1 | 11/2015 | Quan et al. | |
| 2016/0325082 A1* | 11/2016 | Kato | A61M 37/0015 |
| 2017/0319393 A1* | 11/2017 | Kato | A61M 37/0015 |

FOREIGN PATENT DOCUMENTS

| | | |
|---|---|---|
| JP | 2008-543359 A | 12/2008 |
| JP | 2014-28108 A | 2/2014 |
| WO | WO 2015/111672 A1 | 7/2015 |

\* cited by examiner

TRANSDERMAL ADMINISTRATION DEVICE

CROSS-REFERENCE TO RELATED APPLICATIONS

The present application is a continuation of International Application No. PCT/JP2016/050847, filed Jan. 13, 2016, which is based upon and claims the benefits of priority to Japanese Application No. 2015-013559, filed Jan. 27, 2015. The entire contents of these applications are incorporated herein by reference.

BACKGROUND OF THE INVENTION

Field of the Invention

The present invention relates to transdermal administration devices used for drug administration.

Discussion of the Background

As a method of administration of a drug into the body via the skin, use of a transdermal administration device having an administration part such as a microneedle is known. The microneedle includes a plurality of needle-shaped projections formed on the surface of a substrate. In addition to the microneedle, the transdermal administration device further includes an adhesive sheet for fixing the microneedle to the skin, a cover that protects the microneedle, and the like. The adhesive surface of the adhesive sheet is adhered to the back surface of the substrate and extends outward from the substrate. When the substrate is pressed against the skin with the surface of the substrate facing the skin, the adhesive surface of the adhesive sheet which extends outward from the substrate is affixed to the skin. Accordingly, the microneedle is fixed to the skin. At this time, the projections formed on the surface of the substrate pierce the skin to create holes, through which a drug is delivered into the body (for example, see JP-A-2014-28108).

SUMMARY OF THE INVENTION

According to an aspect of the present invention, a transdermal administration device including an administration member including a substrate having a first surface and a second surface opposite to the first surface, and a projection protruding from the first surface, a first adhesive sheet adhered to the second surface and extending outward from the second surface, a second adhesive sheet adhered to the first adhesive sheet on an opposite side of the substrate and extending outward from the first adhesive sheet, and a cover including a main body configured to cover the administration member and the first adhesive sheet, and a flange extending outward from an edge of the main body, the flange being adhered to a portion of the second adhesive sheet which extends outside the first adhesive sheet. The main body and the flange form a structure body including a remaining portion which includes at least a portion of the flange and is configured to remain on the second adhesive sheet, a tear-off portion which includes at least a portion of the main body and is configured to be separated from the remaining portion upon use of the transdermal administration device, and a tear-off assistance portion configured to facilitate formation of a cut for separating the tear-off portion from the remaining portion.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

The embodiments will now be described with reference to the accompanying drawings, wherein like reference numerals designate corresponding or identical elements throughout the various drawings.

With reference to FIGS. 1 to 9, an embodiment of a transdermal administration device will be described.

<Overall Configuration of Transdermal Administration Device>

Figure 1:
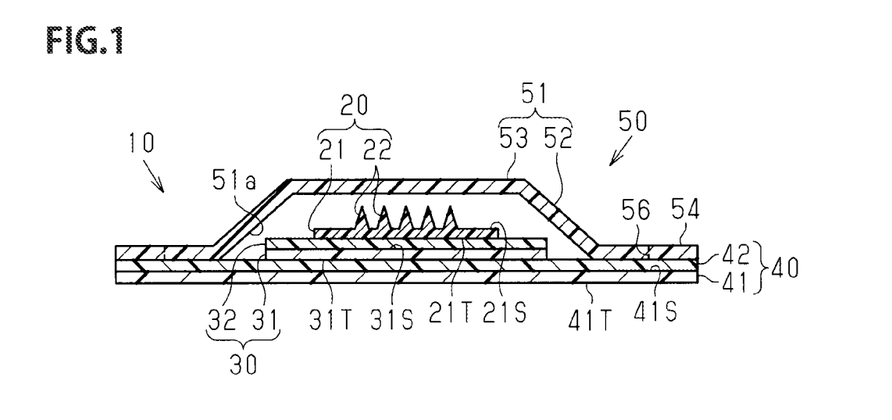
FIG. 1 is a cross-sectional view which illustrates a cross-sectional structure of a transdermal administration device of an embodiment.
Figure 2:
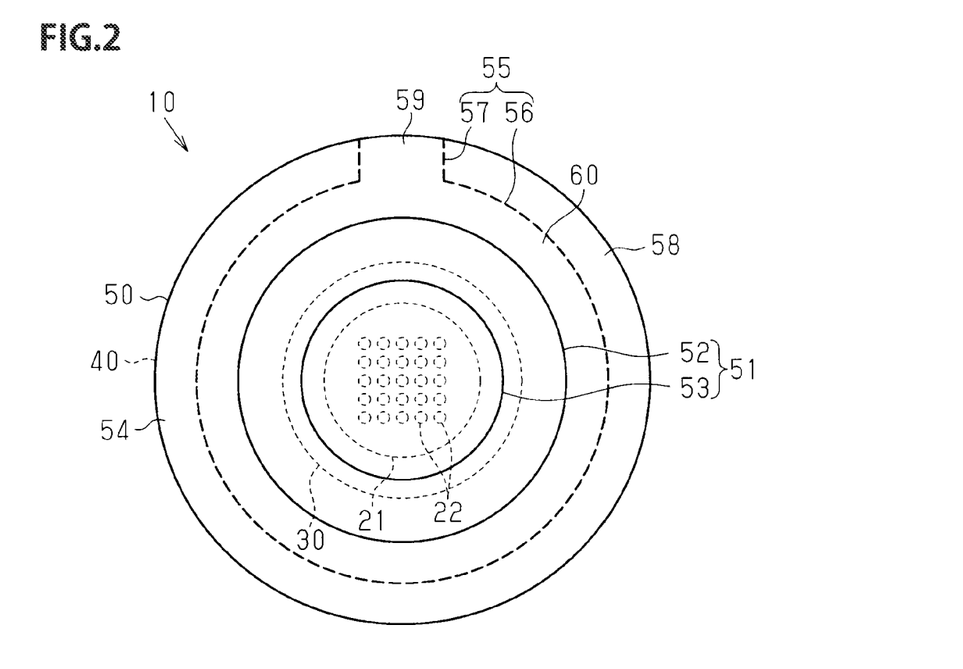
FIG. 2 is a plan view which illustrates a plan structure of a transdermal administration device of an embodiment.

With reference to FIGS. 1 and 2, an overall configuration of a transdermal administration device will be described.

As shown in FIG. 1, a transdermal administration device 10 includes a microneedle 20 which is an example of an administration member, a first adhesive sheet 30, a second adhesive sheet 40, a cover 50.

The microneedle 20 includes a plate-shaped substrate 21 and a projection 22 protruding from the substrate 21. The substrate 21 has a first surface 21S on which the projections 22 are formed and a second surface 21T which is a surface opposite to the first surface 21S. The first surface 21S supports the bases of the projections 22. The outer shape of the substrate 21 as viewed in a direction perpendicular to the first surface 21S is not specifically limited, and may be a circle, oval or rectangle.

The projection 22 may be a pyramid or cone shape. Further, the projection 22 may be a shape which does not have a pointed tip, for example, a cylinder or prism shape. Further, the projection 22 may be a shape composed of a combination of two or more three dimensional shapes, for example, a cone stacked on a cylinder. In other words, the projection 22 may be any shape that can pierce the skin. Moreover, the piercing projection 22 may have a narrow portion or shoulder, or a groove or hole formed on the side wall.

The number of projections 22 is not specifically limited, but is one or more. When the microneedle 20 includes a plurality of projections 22, the plurality of projections 22 may be arranged regularly or irregularly on the first surface 21S of the substrate 21. For example, the plurality of projections 22 is arranged in a matrix or concentric pattern.

The first adhesive sheet 30 includes a first base sheet 31 and a first adhesive layer 32. The first base sheet 31 includes a first covered surface 31S and a first exposed surface 31T which is a surface opposite to the first covered surface 31S. The first adhesive layer 32 covers the entire first covered surface 31S. A surface of the first adhesive layer 32 opposite to a surface that is in contact with the first base sheet 31 is adhered to the second surface 21T of the substrate 21. Accordingly, the substrate 21 of the microneedle 20 is adhered to the first adhesive sheet 30. In the present embodiment, a structure referred to as a "sheet" includes a sheet like structure and a film like structure. That is, a structure referred to as a "sheet" includes a flexible, thin and expanded structure, and the thickness of the structure is not limited.

The outer shape of the first adhesive sheet 30 is larger than the substrate 21 when viewed in the direction perpendicular to the first surface 21S of the substrate 21. In other words, the first adhesive layer 32 of the first adhesive sheet 30 extends outward from the substrate 21 with the adhesive surface exposed when viewed in the direction perpendicular to the first surface 21S. The outer shape of the first adhesive sheet 30 is not specifically limited, and may be, for example, a circle, oval or rectangle.

The second adhesive sheet 40 includes a second base sheet 41 and a second adhesive layer 42. The second base sheet 41 includes a second covered surface 41S and a second exposed surface 41T which is a surface opposite to the second covered surface 41S. The second adhesive layer 42 covers the entire second covered surface 41S. A surface of the second adhesive layer 42 opposite to a surface that is in contact with the second base sheet 41 is adhered to the first exposed surface 31T of the first base sheet 31. Accordingly, the first adhesive sheet 30 is adhered to the second adhesive sheet 40. The first exposed surface 31T of the first base sheet 31 is a surface of the first adhesive sheet 30 opposite to a surface that is in contact with the second surface 21T of the substrate 21.

The outer shape of the second adhesive sheet 40 is larger than the first adhesive sheet 30 when viewed in the direction perpendicular to the first surface 21S of the substrate 21. In other words, the second adhesive layer 42 of the second adhesive sheet 40 extends outward from the first adhesive sheet 30 with the adhesive surface exposed when viewed in the direction perpendicular to the first surface 21S. The outer shape of the second adhesive sheet 40 is not specifically limited, and may be a circle, oval or rectangle.

In the above configuration, the adhesiveness of the second adhesive layer 42 to the first base sheet 31 is set to be lower than the adhesiveness of the first adhesive layer 32 to human skin and lower than the adhesiveness of the first adhesive layer 32 to the substrate 21. The second adhesive layer 42 is adhered to the first base sheet 31 by an adhesive force of such a degree that the second adhesive sheet 40 can be peeled off from the first adhesive sheet 30 by the force of a human hand.

The cover 50 is a container that is disposed to cover the microneedle 20 and the first adhesive sheet 30. The cover 50 includes a main body 51, and the main body 51 is composed of a tubular member 52 having a tubular shape such as a cylindrical or quadrangular cylindrical shape, and an upper plate 53 having a plate shape that closes one of two ends of the tubular member 52. The tubular member 52 has an inner diameter which increases toward the end away from the upper plate 53 such that the inner side surface of the main body 51 defines a housing space 51a that houses the microneedle 20. Further, the cover 50 includes a flange 54 that extends outward from the entire circumference of one of two ends of the tubular member 52, which is located opposite to the end having the upper plate 53. That is, the flange 54 has an annular plate shape that extends outward from the edge of the main body 51.

The main body 51 covers the microneedle 20 and the first adhesive sheet 30 from above the tips of the projections 22 to the substrate 21 of the microneedle 20 such that the microneedle 20 and the first adhesive sheet 30 are disposed in the housing space 51a. That is, the cover 50, and the microneedle 20 and the first adhesive sheet 30 are configured such that one of two surfaces of the upper plate 53 which is oriented inside the housing space 51a faces the first surface 21S of the substrate 21 and the adhesive surface of the first adhesive layer 32 which extends outward from the substrate 21.

The outer shape of the tubular member 52 formed by the outer peripheral edge of the tubular member 52 is larger than the outer shape of the first adhesive sheet 30 and smaller than the outer shape of the second adhesive sheet 40 when viewed in the direction perpendicular to the first surface 21S of the substrate 21. One of the surfaces of the flange 54 which is located opposite to the upper plate 53 is adhered to the second adhesive layer 42 of the second adhesive sheet 40 which extends outward from the first adhesive sheet 30. In other words, the second adhesive sheet 40 closes the housing space 51a. The outer edge of the second adhesive sheet 40 preferably overlaps the outer edge of the flange 54 when viewed in the direction perpendicular to the first surface 21S of the substrate 21.

In the above configuration, the flange 54 is adhered to the second adhesive layer 42 by an adhesive force of such a degree that the flange 54 can be peeled off from the second adhesive sheet 40 by the force of a human hand.

The main body 51 may be any shape that defines the housing space 51a as a space for housing the microneedle 20 and the first adhesive sheet 30. The tubular member 52 may have a constant inner diameter, or the main body 51 may be formed in a shape, for example, a hemisphere shape, which is not composed of separate parts such as the tubular member 52 and the upper plate 53.

As shown in FIG. 2, a weakened portion 55, which is an example of a tear-off assistance portion, is formed on the flange 54 as viewed in a direction perpendicular to the upper plate 53 outside the cover 50, that is, in the direction perpendicular to the first surface 21S of the substrate 21. The weakened portion 55 is the portion of the cover 50 having a shear strength lower than that of the other portions. For example, the weakened portion 55 is implemented by perforation. That is, the weakened portion 55 is a portion which is easily torn by an external force compared with other portions of the cover 50.

Figure 3:
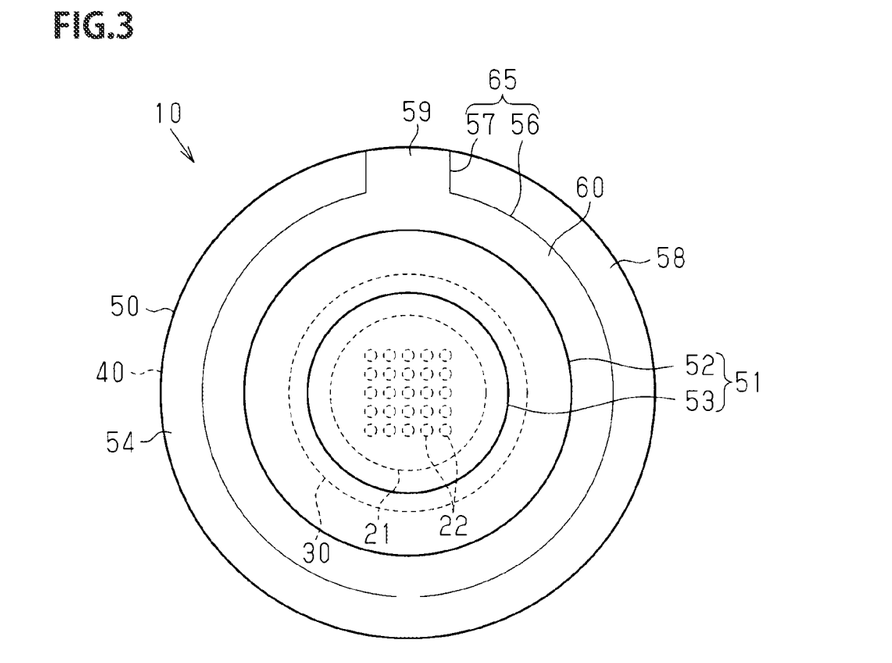
FIG. 3 is a plan view which illustrates another example of a plan structure of a transdermal administration device of an embodiment.

As another example of the weakened portion instead of the perforation, the weakened portion may be the portion of the flange 54 having a reduced thickness compared with the remaining part of the weakened portion. Further, the weakened portion may be a portion of the flange 54 which is partially cut in the thickness direction by half cutting processing or the like. FIG. 3 illustrates an example of a configuration having the weakened portion formed by partially cutting the flange 54 in the thickness direction. The weakened portion 65, which is indicated by the thin line in FIG. 3, is the portion of the flange 54 which is partially cut from the surface of the flange 54 to around the middle in the thickness direction.

Further, the weakened portion may be a combination of the above perforation, the portion of the flange 54 having a reduced thickness, and a portion of the flange 54 partially cut in the thickness direction.

The weakened portion 55 shown in FIG. 2 is configured with a surrounding portion 56 and starting point-forming portions 57. The surrounding portion 56 is disposed along the circle surrounding the main body 51 when viewed in the direction perpendicular to the first surface 21S of the substrate 21, and both ends of the surrounding portion 56 are spaced from each other. The surrounding portion 56 is disposed at the radial center of the flange 54. The starting point-forming portions 57 linearly extend from the respective ends of the surrounding portion 56 to the outer edge of the flange 54.

Moreover, as shown in FIG. 3, the circle formed by the surrounding portion 56 may be separated at a position other than the ends that are connected to the starting point-forming portions 57.

The portion of the flange 54 located outside the weakened portion 55 as viewed in the direction perpendicular to the first surface 21S of the substrate 21 is a remaining portion 58. The portion of the cover 50 except for the remaining portion 58, that is, the portion surrounded by the weakened portion 55 is a tear-off portion 60. The portion of the flange 54 located between the starting point-forming portions 57 is a starting portion 59 which is a part of the tear-off portion 60. The remaining portion 58 is positioned along the outer edge of the second adhesive sheet 40 when viewed in the direction perpendicular to the first surface 21S of the substrate 21, and the remaining portion 58 and the first adhesive sheet 30 are spaced from each other.

In the above configuration, when the cover 50 is torn off at the weakened portion 55, the tear-off portion 60 is separated from the remaining portion 58. The remaining portion 58 is left on the second adhesive sheet 40. At this time, a cut is created between the remaining portion 58 that remains on the second adhesive sheet 40 and the tear-off portion 60 so that the weakened portion 55 facilitates creation of a cut on the cover 50. That is, the remaining portion 58 is the portion to be left on the second adhesive sheet 40, and the tear-off portion 60 is the portion not to be separated from the remaining portion 58. The tear-off portion 60 includes the entire main body 51.

<Detailed Configuration of Microneedle>

Figure 4:
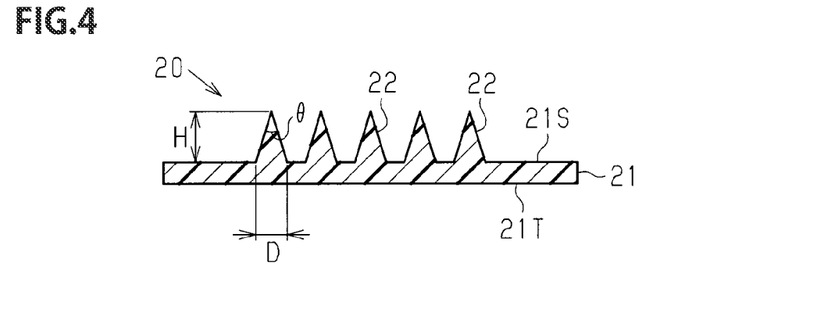
FIG. 4 is a cross-sectional view which illustrates a cross-sectional structure of an administration member of a transdermal administration device of an embodiment.

With reference to FIG. 4, a detailed configuration of the microneedle 20 will be described, focusing on a configuration of the projection 22.

As shown in FIG. 4, the projection 22 has a length H which is a length from the first surface 21S to the tip of the projection 22 in the direction perpendicular to the first surface 21S of the substrate 21. The length H of the projection 22 is preferably in the range of 10 μm or more and 1000 μm or less, and is determined depending on the depth required for the hole to be punctured by the projection 22 within the above range. When the puncture target is the human skin and the depth of the hole is designed to be in the stratum corneum, the length H is preferably in the range of 10 μm or more and 300 μm or less, more preferably in the range of 30 μm or more and 200 μm or less. When the depth of the hole is designed to penetrate through the stratum corneum and not to reach the nerve, the length H is preferably in the range of 200 μm or more and 700 μm or less, more preferably in the range of 200 μm or more and 500 μm or less, and further more preferably in the range of 200 μm or more and 300 μm or less. When the depth of the hole is designed to reach the dermis, the length H is preferably in the range of 200 μm or more and 500 μm or less. When the depth of the hole is designed to reach the epidermis, the length H is preferably in the range of 200 μm or more and 300 μm or less.

The projection 22 has a width D, which is a maximum length of the projection 22 in a direction parallel with the first surface 21S of the substrate 21. For example, when the projection 22 has a regular quadrangular pyramid or regular quadrangular prism shape, the width D of the projection 22 is a diagonal length of a square defined by the bottom of the projection 22 on the first surface 21S of the substrate 21. Further, when the projection 22 has a cone or cylinder shape, the width D of the projection 22 is a diameter of a circle defined by the bottom of the projection 22. Preferably, the width D of the projection 22 is in the range of 1 μm or more and 300 μm or less.

An aspect ratio A which is a ratio of the length H to the width D of the projection 22 (A=H/D) is preferably in the range of 1 or more and 10 or less.

When the tip of the projection 22 is formed in a pointed shape and the hole is formed by the projection 22 to penetrate the stratum corneum, the tip angle θ of the projection 22 is preferably in the range of 5° or more and 30° or less, more preferably in the range of 10° or more and 20° or less. The tip angle θ is a maximum angle made by the tip of the projection 22 in a cross section perpendicular to the first surface 21S of the outer substrate 21. For example, when the projection 22 has a regular quadrangular pyramid shape, the tip angle θ of the projection 22 is an apex angle of a triangle having a diagonal line of a square defined by the bottom of the projection 22 as a base and the apex of the regular quadrangular pyramid as an apex.

The width D, the aspect ratio A, and the tip angle θ of the projection 22 are determined depending on the volume or the like required for the hole to be formed by the projection 22. When the length H, the width D, the aspect ratio A, and the tip angle θ are within the above ranges, the shape of the projection 22 is in the form suitable for forming a hole into the skin.

<Production Method of Transdermal Administration Device>

A production method of the transdermal administration device 10 will be described, including materials and production methods of components of the transdermal administration device 10.

The microneedle 20 is preferably made of a biocompatible material. Examples of the biocompatible material include metals such as silicon, stainless steel, titanium, and manganese, and thermoplastic resins such as medical grade silicone, polylactic acid, polyglycol acid, polycarbonate, and cyclic olefin copolymer. However, the biocompatible material that can be used as a material forming the microneedle 20 is not limited to the above materials.

Alternatively, the microneedle 20 may be made of a water-soluble material that dissolves in water contained in the skin. The water-soluble material may be a water-soluble polymer or polysaccharide. Examples of the water-soluble polymer include carboxymethyl cellulose (CMC), methylcellulose (MC), hydroxylpropyl cellulose (HPC), hydroxypropyl methylcellulose (HPMC), polyvinyl alcohol (PVA), polyacrylic acid polymer, polyacrylic amide (PAM), polyethylene oxide (PEO), pullulan, alginate, pectin, chitosan, chitosan succinamide, and oligochitosan. Among the above materials, chitosan, chitosan succinamide, carboxymethyl cellulose (CMC), hydroxylpropyl cellulose (HPC), hydroxypropyl methylcellulose (HPMC) are advantageously used since they have high biological safety. Further, the disaccharide may be trehalose or maltose. However, the water-soluble material used as a material forming the microneedle 20 is not limited to the above materials.

Further, the substrate 21 and the projection 22 may be made of a material having the same composition, or materials having different compositions.

Among the above materials, the microneedle 20 is preferably made of a material that dissolves in water contained in the skin, that is, a water-soluble material. The microneedle 20 made of a water soluble material is easily deformed due to flexibility, and often difficult to handle. In contrast, when the transdermal administration device 10 of the present embodiment is configured to have a microneedle 20 made of a water soluble material, handling of the transdermal administration device 10 as a whole is improved regardless of flexibility of the microneedle 20. Accordingly, the microneedle 20 can be easily handled.

A drug administered by the microneedle 20 may be any kind of drug as long as it is effective when administered into the skin. A drug may be applied on the surface of the projection 22 and delivered into the skin as the projection 22 creates a hole in the skin, or alternatively, a drug may be contained inside the projection 22 and delivered into the skin as the projection 22 dissolves when the projection 22 is made of a soluble material as described above. Alternatively, when the projection 22 has a groove or hole, a drug may be filled into the groove or hole and may be delivered into the skin as the projection 22 creates a hole in the skin. Further, a liquid drug may be applied on the skin before or after the projection 22 is pierced into the skin so that the drug is delivered into the skin through a hole created by the projection 22. Moreover, a drug may be applied by combinations of these techniques. When the projection 22 is made of a soluble material, a water soluble polymer that constitutes the projection 22 may serve as a drug.

Examples of a drug include various types of proteins, pharmacologically active agents, or cosmetic compositions, which are appropriately selected depending on the purpose.

Examples of a pharmacologically active agent include vaccines such as influenza vaccine, pain relievers for cancer patients, insulin, biologics, gene therapy agents, injections, oral agents, skin application preparations and the like. In transdermal administration using the microneedle 20, a drug is administered into a hole created in the skin. Therefore, transdermal administration using the microneedle 20 can be applied to not only administration of the pharmacologically active agents used in the conventional transdermal administration, but also administration of pharmacologically active agents that require hypodermic injection. In particular, transdermal administration using the microneedle 20 is suitable for administration of an injection medication such as vaccines for children since it does not cause pain to a patient during administration. Further, transdermal administration using the microneedle 20 is suitable for administration of an oral medication for children who have difficulty in swallowing an oral medication since it does not require a patient to swallow a drug during administration.

Cosmetic compositions are compositions for use as cosmetics or beauty products. Examples of a cosmetic composition include humectants, colorants, fragrance, and physiologically active agents exhibiting cosmetic effects such as improvement effect on wrinkles, acne, stretch marks or the like, and improvement effect on hair loss or the like. When an aromatic material is used as a cosmetic composition, a fragrance can be imparted to the microneedle 20. Accordingly, a transdermal administration device 10 suitable for use as a beauty product can be obtained.

The microneedle 20 can be produced by various known techniques depending on the material forming the microneedle 20. For example, when the microneedle 20 is made of a resin, the microneedle 20 can be produced by injection molding, extrusion molding, imprinting, hot embossing, casting or the like. Further, the microneedle 20 can also be produced by microprocessing techniques such as lithography, wet etching, dry etching, sand blasting, laser processing, and micromachining.

Alternatively, the microneedle 20 may be produced by producing an original plate for the microneedle 20 by the above-mentioned techniques, and producing an intaglio plate having an inverted shape of projections and recesses of the original plate by using a known shape-transfer technique, and filling a forming material for the microneedle 20 into the intaglio plate.

For example, when the microneedle 20 is made of a water soluble polymer, a material solution containing a water soluble polymer and a drug is prepared and supplied into the intaglio plate. The way of supplying the material solution into the intaglio plate may be appropriately selected from known methods taking into consideration the shape or size of the intaglio plate or the like. The material solution can be supplied by methods such as spin coating, use of dispenser, casting, and ink jetting. When the material solution in the intaglio plate is dried and solidified, a molded product provided as the microneedle 20 is formed and removed from the intaglio plate to thereby obtain the microneedle 20.

For example, when the microneedle 20 is made of a thermoplastic resin, the microneedle 20 may be formed by placing a sheet-shaped thermoplastic resin on the intaglio plate and filling the intaglio plate with the thermoplastic resin by thermal pressing or the like.

The second surface 21T of the substrate 21 of the microneedle 20 thus formed is adhered to the first adhesive layer 32 of the first adhesive sheet 30, and the first exposed surface 31T of the first base sheet 31 is adhered to the second adhesive layer 42 of the second adhesive sheet 40. Then, the cover 50 having the weakened portion 55 is placed to cover the microneedle 20 and the first adhesive sheet 30, and the flange 54 is adhered to the second adhesive layer 42 to thereby form the transdermal administration device 10.

Materials for the first adhesive sheet 30 and the second adhesive sheet 40 are not specifically limited, but the base sheets 31 and 41 may be formed of a resin sheet made of polyolefin resin such as polyethylene and polypropylene, polyester resin such as nylon and polyethylene terephthalate, or polyvinyl chloride, polyvinylidene chloride, polyvinyl alcohol or the like. Further, the adhesive layers 32 and 42 may be made of silicone adhesive, rubber adhesive, epoxy adhesive or acrylic adhesive or the like, and the adhesiveness of the second adhesive layer 42 to the first base sheet 31 is set to be lower than the adhesiveness of the first adhesive layer 32 to the human skin and lower than the adhesiveness of the first adhesive layer 32 to the substrate 21.

In the transdermal administration device 10 of the present embodiment, materials for the first adhesive sheet 30 and the second adhesive sheet 40, that is, materials for the base sheets 31 and 41 and materials for the adhesive layers 32 and 42 are not limited to the above materials.

Materials for the cover 50 are not specifically limited, but may be polyolefin resin such as polyethylene and polypropylene, polyester resin such as nylon and polyethylene terephthalate, or acrylic resin such as polystyrene. Materials for the cover 50 are preferably those having rigidity higher than that of the second adhesive sheet 40.

In the transdermal administration device 10 of the present embodiment, materials for the cover 50 are not limited to the above materials.

<Effects>

Figure 5:
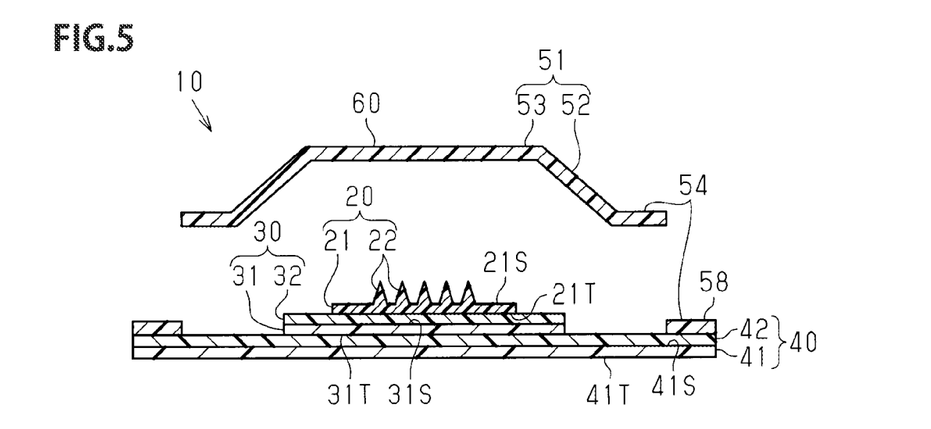
FIG. 5 is a view which illustrates a usage of a transdermal administration device of an embodiment, and the view illustrates that a tear-off portion is removed with a remaining portion being left.
Figure 6:
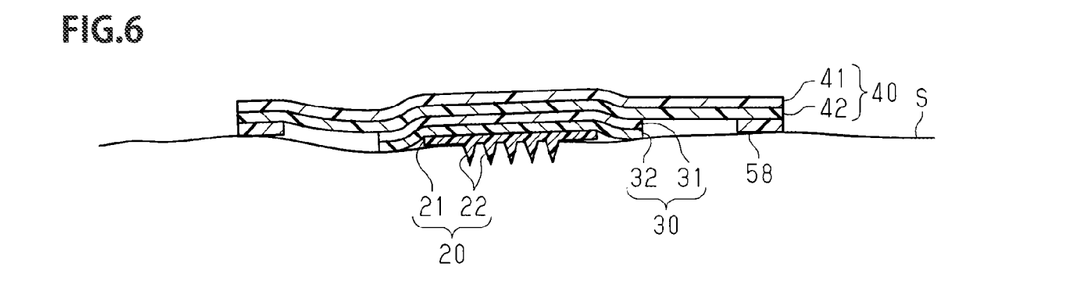
FIG. 6 is a view which illustrates a usage of a transdermal administration device of an embodiment, and the view illustrates that a first adhesive sheet is affixed to the skin surface.
Figure 7:
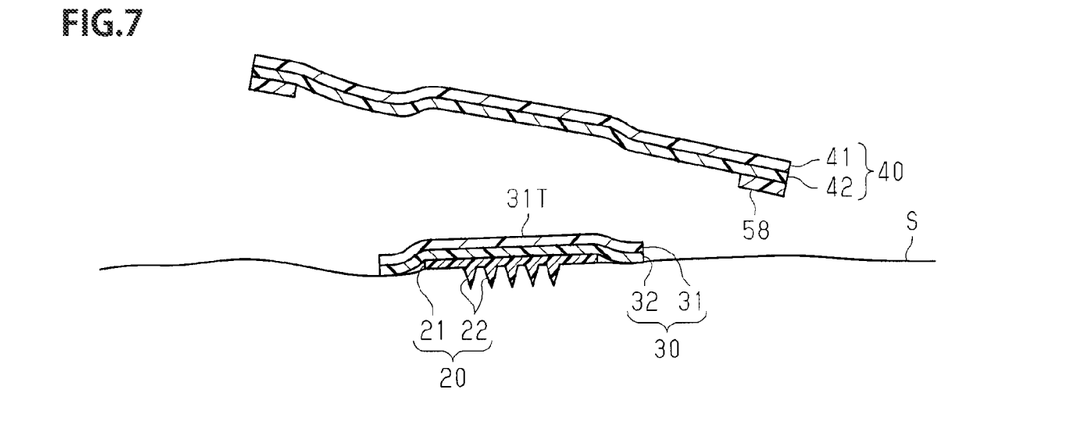
FIG. 7 is a view which illustrates a usage of a transdermal administration device of an embodiment, and the view illustrates that a second adhesive sheet is peeled off.

With reference to FIGS. 5 to 7, effects of the transdermal administration device 10 will be described while describing the usage of the transdermal administration device 10.

In use of the transdermal administration device 10, the user peels off the end of the starting portion 59 from the second adhesive sheet 40 and pulls up the starting portion 59. Accordingly, a cut is formed from the starting point-forming portion 57 to the surrounding portion 56 along the weakened portion 55 to cut off the cover 50 so that the tear-off portion 60 which is the portion of the cover 50 surrounded by the weakened portion 55 is separated from the remaining portion 58 and peels off from the second adhesive sheet 40.

As a result, as shown in FIG. 5, the remaining portion 58 remains on the second adhesive sheet 40 along the outer edge of the second adhesive sheet 40, and the microneedle 20 and the first adhesive sheet 30 are exposed. After that, the user brings the transdermal administration device 10 to a position on the body of the user where the drug is to be administered. Here, the remaining portion 58, which is a portion of the cover 50, is disposed on the second adhesive sheet 40. Accordingly, the portion of the transdermal administration device 10 which is held by the user has high rigidity compared with the case in which the cover 50 is completely removed. As a result, inadvertent adhesion between the adhesive surfaces of the first adhesive sheet 30 and the second adhesive sheet 40 can be prevented in the period from when the tear-off portion 60 that covers the microneedle 20 and the first adhesive sheet 30 is removed to when the adhesive surface of the first adhesive sheet 30 is affixed to the skin. This improves handling of the transdermal administration device 10, that is, the transdermal administration device 10 can be easily handled.

In particular, since the remaining portion 58 is disposed along the outer edge of the second adhesive sheet 40, the end of the transdermal administration device 10 as viewed in the direction perpendicular to the first surface 21S of the substrate 21 has high rigidity compared with the case in which the remaining portion 58 remains inside the outer edge of the second adhesive sheet 40. This facilitates the user to easily support the transdermal administration device 10, and accordingly, the transdermal administration device 10 can be easily handled. As a result of improvement in handling of the transdermal administration device 10, deformation of the projection 22 can be reduced by protecting the projection 22 from being inadvertently touched by the user before the adhesive surface of the first adhesive sheet 30 is affixed to the skin.

As shown in FIG. 6, the user presses the substrate 21 against a skin surface S with the projections 22 being oriented to the skin surface S at a position where the drug is to be administered, and affixes the adhesive surface of the first adhesive sheet 30 exposed outside the substrate 21 to the skin surface S.

In the transdermal administration device 10, the portion of the second adhesive sheet 40 where the remaining portion 58 is not disposed, more specifically, the portion where the second adhesive layer 42 of the second adhesive sheet 40 is exposed between the first adhesive sheet 30 and the remaining portion 58, is highly flexible as with the case where the cover 50 is completely peeled off. Accordingly, even if the remaining portion 58 is left, there is less difficulty in pressing the substrate 21 against the skin surface S and in affixing the first adhesive sheet 30 to the skin surface S. Compared with the configuration having high rigidity of the second adhesive sheet 40 itself, the transdermal administration device 10 in the present embodiment is superior in handling while facilitating fixation of the microneedle 20 to the curved skin surface S.

In addition, fixation of the microneedle 20 to the skin surface S becomes easier with increase in the distance between the remaining portion 58 and the substrate 21 of the microneedle 20, that is, the size of the exposed portion of the adhesive sheets 30 and 40 between the remaining portion 58 and the substrate 21 of the microneedle 20.

As shown in FIG. 7, after the microneedle 20 is fixed to the skin, the user peels off the second adhesive sheet 40 together with the remaining portion 58 from the first adhesive sheet 30. Since the adhesiveness of the second adhesive layer 42 to the first base sheet 31 is lower than the adhesiveness of the first adhesive layer 32 to the skin, the second adhesive sheet 40 can be easily peels off.

Accordingly, the microneedle 20 is fixed to the skin with the first exposed surface 31T of the first base sheet 31 of the first adhesive sheet 30 exposed, and the drug is administered into the skin via the puncture holes created by the projections 22.

As described below, the transdermal administration device 10 of the present embodiment includes both the configuration shown in FIG. 8 and the configuration shown in FIG. 9. As previously described, the transdermal administration device 10 is highly flexible at the portion of the second adhesive layer 42 of the second adhesive sheet 40 exposed between the first adhesive sheet 30 and the remaining portion 58. Except for that portion, the microneedle 20 and the first adhesive sheet 30 may or may not conform to the deformation of the second adhesive sheet 40.

Figure 8:
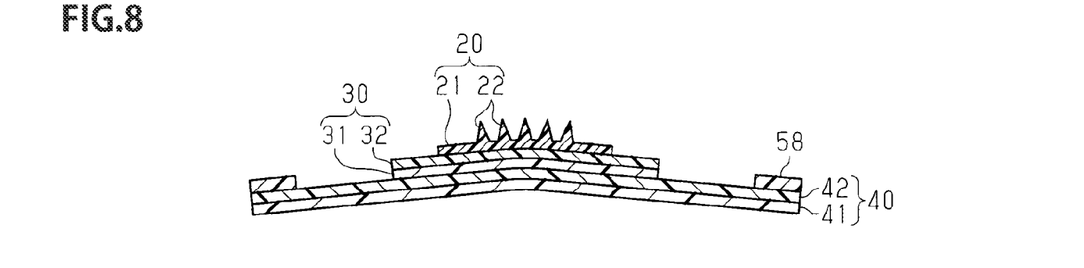
FIG. 8 is a view which illustrates an example in which a transdermal administration device according to an embodiment is deformed.

That is, as shown in FIG. 8, both the microneedle 20 and the first adhesive sheet 30 may have flexibility of a degree that conforms to the deformation of the second adhesive sheet 40. Alternatively, as shown in FIG. 9, the first adhesive sheet 30 or both the microneedle 20 and the first adhesive sheet 30 may not necessarily have flexibility of a degree that conforms to the deformation of the second adhesive sheet 40 so that the microneedle 20 and the first adhesive sheet 30 do not conform to the deformation of the second adhesive sheet 40. In this case, a gap is created between the first adhesive sheet 30 and the second adhesive sheet 40 according to the deformation of the second adhesive sheet 40.

Figure 9:
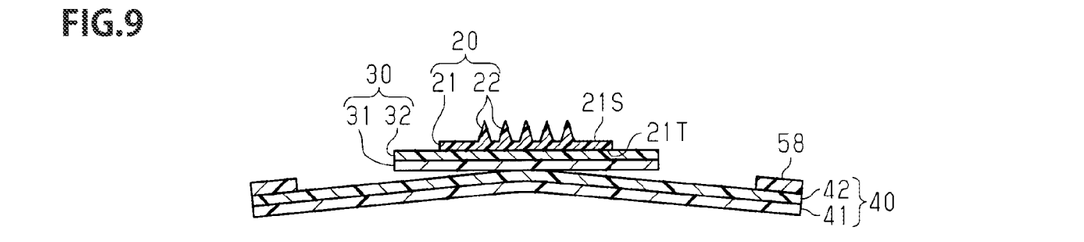
FIG. 9 is a view which illustrates an example in which a transdermal administration device according to an embodiment is deformed.

In the configuration shown in FIG. 8 and the configuration shown in FIG. 9, the deformation of the transdermal administration device 10 may be reversible or non-reversible.

As described above, according to the transdermal administration device 10, the following effects can be achieved.

(1) Creation of the cut along which the tear-off portion 60 including at least part of the main body 51 is separated from the remaining portion 58 including at least part of the flange 54 is facilitated. With this configuration, the remaining portion 58 is left on the second adhesive sheet 40 when the tear-off portion 60 is removed during use of the transdermal administration device 10. As a result, the portion of the transdermal administration device 10 which is held by the user has high rigidity compared with the case where the cover 50 is completely removed. Therefore, handling of the transdermal administration device 10 is improved.

(2) The configuration that facilitates creation of a cut is embodied as the weakened portion 55, the tear-off portion 60 can be easily removed by an external force. In addition, since the tear-off portion 60 is separated from the remaining portion 58 along the weakened portion 55, a separation position can be easily determined.

(3) Since the remaining portion 58 is disposed along the outer edge of the second adhesive sheet 40, the end of the transdermal administration device 10 has high rigidity compared with the case in which the remaining portion 58 remains inside the outer edge of the second adhesive sheet 40. Accordingly, the user can easily support the transdermal administration device 10, and therefore handling of the transdermal administration device 10 is further improved.

(4) Since the remaining portion 58 is part of the flange 54, the tear-off portion 60 includes part of the flange 54. In this configuration, the portion of the tear-off portion 60 which is included in the flange 54 is adhered to the second adhesive sheet 40 before it is removed. Accordingly, before use of the transdermal administration device 10, the tear-off portion 60 can be prevented from being separated from the remaining portion 58 even if an unintentional external force is applied to the transdermal administration device 10.

(5) Since the remaining portion 58 and the first adhesive sheet 30 are spaced when viewed in the direction perpendicular to the first surface 21S of the substrate 21, the portion of the second adhesive sheet 40 which is exposed between the first adhesive sheet 30 and the remaining portion 58 is highly flexible as with the case where the cover 50 is completely peeled off. Accordingly, even if the remaining portion 58 is left after the tear-off portion 60 is removed from the remaining portion 58, there is less difficulty in pressing the substrate 21 against the skin surface S and in affixing the first adhesive sheet 30 to the skin surface S.

(6) Since the adhesiveness of the second adhesive layer 42 to the first base sheet 31 is lower than the adhesiveness of the first adhesive layer 32 to the skin, the second adhesive sheet 40 can be easily peeled off from the first adhesive sheet 30 after the first adhesive sheet 30 is affixed to the skin surface S. Moreover, an effect similar to the above effect can be obtained in the configuration in which the adhesiveness of the second adhesive layer 42 to the first base sheet 31 is lower than the adhesiveness of the first adhesive layer 32 to the substrate 21.

The above embodiment can be implemented with modifications as described below.

Figure 10:
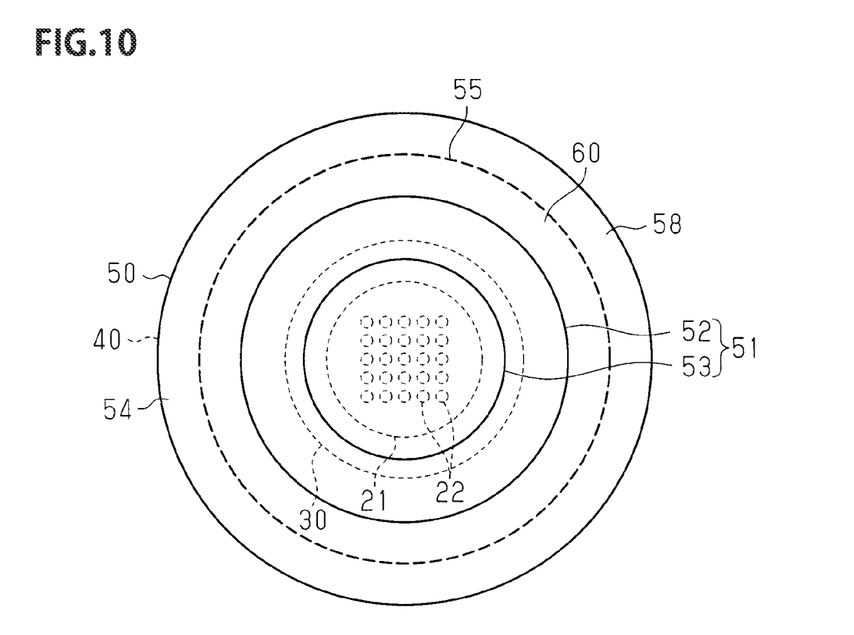
FIG. 10 is a plan view which shows a plan structure of the transdermal administration device of a modification.

In the above embodiment, the cover 50 is not left on the portion of the second adhesive sheet 40 where the starting portion 59 is located. Accordingly, there is a portion that does not include the remaining portion 58 in the outer peripheral area of the second adhesive sheet 40 when viewed in the direction perpendicular to the first surface 21S of the substrate 21. Instead of this configuration, as shown in FIG. 10, the remaining portion 58 may be disposed in the entire outer peripheral area of the second adhesive sheet 40 when viewed in the direction perpendicular to the first surface 21S of the substrate 21. In this case, the weakened portion 55 has an annular shape that surrounds the main body 51 when viewed in the direction perpendicular to the first surface 21S of the substrate 21. In this configuration, a portion serving as a pull-tab which is pulled up by the user, for example, for removal of the tear-off portion 60 surrounded by the weakened portion 55 may be disposed on the tubular member 52, the upper plate 53 or the like. Alternatively, the tear-off portion 60 may be removed by the user grabbing and pulling up the tubular member 52.

In the above embodiment, the surrounding portion 56 that constitutes the weakened portion 55 is disposed at the center in the radial direction of the flange 54. However, the surrounding portion 56 may be disposed at a position offset from the center in the radial direction of the flange 54 or may be disposed at the boundary between the main body 51 and the flange 54. Moreover, in the configuration shown in FIG. 10, the weakened portion 55 may be disposed at the boundary between the main body 51 and the flange 54. In this case, the entire flange 54 serves as the remaining portion 58, and the entire main body 51 serves as the tear-off portion 60.

The remaining portion 58 may be a portion that includes at least part of the flange 54 in the cover 50, or may be a portion that includes part of the main body 51. Moreover, the tear-off portion 60 may be a portion that includes at least part of the main body 51 in the cover 50.

The remaining portion 58 and the first adhesive sheet 30 may be in contact with each other when viewed in the direction perpendicular to the first surface 21S of the substrate 21. For example, in the configuration in which the inner peripheral edge of the flange 54 and the outer peripheral edge of the first adhesive sheet 30 are in contact with each other, and the weakened portion 55 is disposed at the boundary between the main body 51 and the flange 54, the remaining portion 58 and the first adhesive sheet 30 are in contact with each other.

Figure 11:
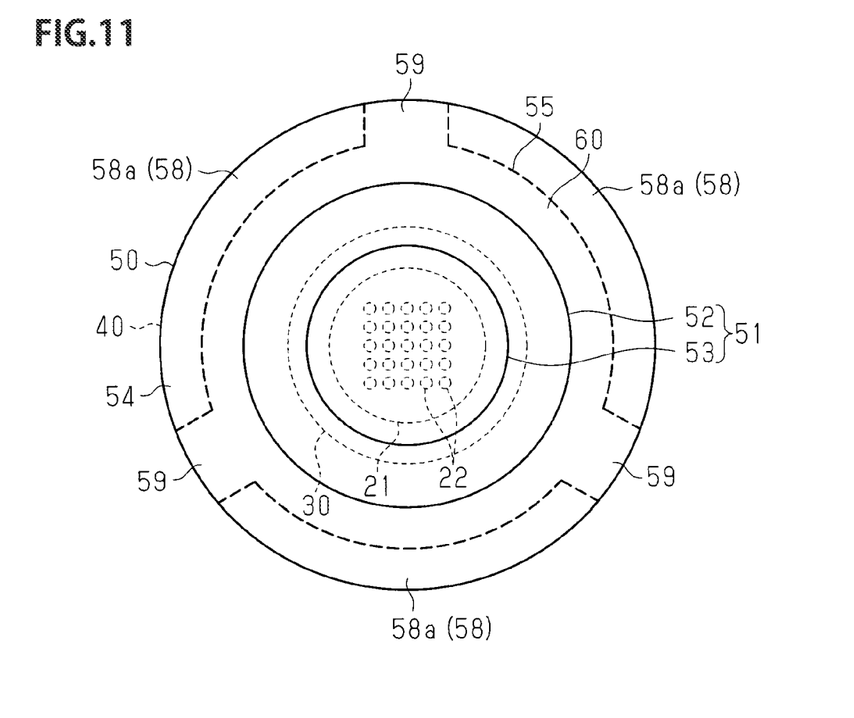
FIG. 11 is a plan view which shows a plan structure of the transdermal administration device of a modification.

In the above embodiment, the remaining portion 58 in the cover 50 is a continuous portion. However, the remaining portion 58 may be a plurality of separate portions. For example, as shown in FIG. 11, a plurality of starting portions 59 may be disposed along the periphery of the flange 54. In the example shown in FIG. 11, three starting portions 59 are disposed. The remaining portion 58 is made up of three remaining pieces 58a which are located between the starting portions 59 disposed along the periphery of the flange 54. However, with increase in the area occupied by the remaining portion 58 in the outer peripheral area of the second adhesive sheet 40 when viewed in the direction perpendicular to the first surface 21S of the substrate 21, the user can more easily support the transdermal administration device 10 and more improved handling of the transdermal administration device 10 is achieved.

The remaining portion 58 may be spaced from the outer edge of the second adhesive sheet 40, and the remaining portion 58 may be disposed inside the outer edge of the second adhesive sheet 40 when viewed in the direction perpendicular to the first surface 21S of the substrate 21. In this configuration as well, handling of the transdermal administration device 10 is improved compared with the configuration in which the cover 50 is completely removed.

The configuration that facilitates creation of a cut for separating the tear-off portion 60 from the remaining portion 58 is not limited to the configuration in which the tear-off portion 60 is surrounded by the weakened portion 55. For example, a cut which is an example of a tear-off assistance portion may be provided only in a region adjacent to the starting portion 59 so that the cover 50 is torn off from the cut when the starting portion 59 is pulled up. Alternatively, a cut tape which is an example of a tear-off assistance portion for cutting the cover 50 may be adhered to the cover 50 so that the cover 50 is cut when the starting portion 59 bonded to the cut tape is pulled up.

The shape of the projection 22 of the administration member is not limited to a needle-shape, that is, a shape extending in the direction perpendicular to the first surface 21S of the substrate 21. The shape of the projection 22 may be a blade-shape, that is, a linear shape in which the projection 22 extends in an extending direction along the first surface 21S of the substrate 21 and a distal portion of the projection extends not in the direction perpendicular to the first surface 21S of the substrate 21 but in a direction, for example, extending along the extending direction. For example, the projection 22 may be formed as a triangular prism shape that extends along the extending direction while one of three rectangular side surfaces of the triangular prism is in contact with the substrate 21 and the side of the triangular prism that partitions the other two side surfaces serves as a tip of the projection 22.

For smooth administration of a drug, it is preferred that projections are sufficiently inserted into the skin so that the holes are created into the desired depth suitable for administration of the drug. For this purpose, it is desired to fix the microneedle to the skin surface and maintain the fixation. Accordingly, attempts have been made to increase conformity of the substrate and the adhesive sheet to the shape of the skin surface.

For example, the flexibility of the adhesive sheet is usually improved by decreasing a thickness of the sheet or decreasing a rigidity of the sheet, and thus the conformity is improved. However, if the flexibility of the adhesive sheet is high, the adhesive sheet may be inadvertently folded before the adhesive surface of the adhesive sheet is affixed to the skin surface, leading to adhesion together of the adhesive surfaces. As a result, in the period from when the cover is removed to when the adhesive surface is affixed to the skin surface, handling of the transdermal administration device is impaired.

An aspect of the present invention is to provide a transdermal administration device with easiness in handling.

In order to solve the above problem, a transdermal administration device according to an aspect of the invention includes: an administration member including a substrate having a first surface and a second surface which is a surface opposite to the first surface, and a projection protruding from the first surface; a first adhesive sheet adhered to the second surface, the first adhesive sheet extending outward from the second surface; a second adhesive sheet adhered to a surface of the first adhesive sheet opposite to a surface which is in contact with the second surface, the second adhesive sheet extending outward from the first adhesive sheet; and a cover which covers the administration member and the first adhesive sheet. The cover includes: a main body that covers the administration member and the first adhesive sheet; and a flange which extends outward from an edge of the main body, the flange being adhered to a portion of the second adhesive sheet which extends outside the first adhesive sheet, and a structure composed of the main body and the flange includes: a remaining portion which includes at least a portion of the flange and is designed to be left on the second adhesive sheet; a tear-off portion which includes at least a portion of the main body and is designed to be separated from the remaining portion; and a tear-off assistance portion which facilitates creation of a cut for separating the tear-off portion from the remaining portion.

With this configuration, the remaining portion which is part of the cover is left on the second adhesive sheet when the tear-off portion which covers the administration member is separated and removed from the remaining portion during use of the transdermal administration device. As a result, the portion of the transdermal administration device which is held by the user has high rigidity compared with the case where the cover is completely removed. Therefore, in the period from when the tear-off portion is removed to when the adhesive surface of the first adhesive sheet is affixed to the skin, inadvertent adhesion between the adhesive surfaces of the first adhesive sheet and the second adhesive sheet can be prevented. This improves handling of the transdermal administration device, that is, the transdermal administration device can be easily handled.

In the above transdermal administration device, the tear-off assistance portion may be a weakened portion which is a portion easily torn off compared with the other portion of the structure.

With this configuration, the tear-off portion is easily removed from the remaining portion. Further, since the tear-off portion is separated from the remaining portion along the weakened portion, a separation position can be easily determined.

The remaining portion may be a portion of the flange, and may be positioned along an outer edge of the second adhesive sheet when viewed in a direction perpendicular to the first surface of the substrate.

With this configuration, the end of the transdermal administration device has high rigidity compared with the case in which the remaining portion remains inside the outer edge of the second adhesive sheet. Accordingly, the user can easily support the transdermal administration device, and therefore handling of the transdermal administration device is further improved. Since the remaining portion is part of the flange, the tear-off portion includes part of the flange. In this configuration, the portion of the tear-off portion which is included in the flange is adhered to the second adhesive sheet before it is removed. Accordingly, before use of the transdermal administration device, the tear-off portion can be prevented from being separated from the remaining portion even if an unintentional external force is applied to the transdermal administration device.

In the above transdermal administration device, the remaining portion and the first adhesive sheet may be spaced from each other when viewed in the direction perpendicular to the first surface of the substrate.

With this configuration, a portion where the second adhesive sheet is disposed between the first adhesive sheet and the remaining portion is highly flexible as with the case where the cover is completely peeled off. Accordingly, even if the remaining portion is left after the tear-off portion is removed from the remaining portion, there is less difficulty in pressing the substrate against the skin surface and in affixing the first adhesive sheet to the skin surface.

In the above transdermal administration device, an adhesiveness of the second adhesive layer to the first base sheet may be lower than the adhesiveness of the first adhesive layer to the skin.

With this configuration, the second adhesive sheet can be easily peeled off from the first adhesive sheet after the first adhesive sheet is affixed to the skin surface.

According to embodiments of the present invention, handling of the transdermal administration device can be improved.

REFERENCE SIGNS LIST

10 . . . Transdermal administration device
20 . . . Microneedle
21 . . . Substrate
21S . . . First surface
21T . . . Second surface
22 . . . Projection
30 . . . First adhesive sheet
31 . . . First base sheet
32 . . . First adhesive layer
40 . . . Second adhesive sheet
41 . . . Second base sheet
42 . . . Second adhesive layer
50 . . . Cover
51 . . . Main body
52 . . . Tubular member
53 . . . upper plate
54 . . . Flange
55, 65 . . . Weakened portion
56 . . . Surrounding portion
57 . . . Starting point-forming portion
58 . . . Remaining portion
59 . . . Starting portion
60 . . . Tear-off portion Obviously, numerous modifications and variations of the present invention are possible in light of the above teachings. It is therefore to be understood that within the scope of the appended claims, the invention may be practiced otherwise than as specifically described herein.

What is claimed is:

1. A transdermal administration device, comprising:
a microneedle comprising a substrate, and a projection protruding from a first surface of the substrate;
a first adhesive sheet comprising a first base sheet and a first adhesive layer such that the first adhesive layer is adhered to a second surface of the substrate on an opposite side of the first surface and that the first base sheet and first adhesive layer are extending outward from the second surface of the substrate;
a second adhesive sheet comprising a second base sheet and a second adhesive layer such that the second adhesive layer is adhered to the first base sheet of the first adhesive sheet and that the second base sheet and second adhesive layer are extending outward from the first adhesive sheet; and
a cover comprising a main body configured to cover the microneedle and the first adhesive sheet, and a flange extending outward from an edge of the main body and adhered to the second adhesive layer of the second adhesive sheet,
wherein the cover is formed such that the main body and the flange form a structure body including a remaining portion which includes at least a portion of the flange and is configured to remain adhered on the second adhesive sheet, a tear-off portion which includes at least a portion of the main body and is configured to be separated from the remaining portion, and a tear-off assistance portion configured to form a cut separating the tear-off portion from the remaining portion.

2. The transdermal administration device of claim 1, wherein the tear-off assistance portion is a weakened portion which is more easily tearable as compared with a rest of the structure body.

3. The transdermal administration device of claim 2, wherein the remaining portion is part of the flange and positioned along an outer edge of the second adhesive sheet when viewed in a direction perpendicular to the first surface of the substrate.

4. The transdermal administration device of claim 3, wherein the remaining portion and the first adhesive sheet are spaced from each other when viewed in the direction perpendicular to the first surface of the substrate.

5. The transdermal administration device of claim 3, wherein the first and second adhesive sheets are formed such that an adhesiveness between the first and second adhesive sheets is lower than an adhesiveness of the first adhesive sheet to skin.

6. The transdermal administration device of claim 2, wherein the remaining portion and the first adhesive sheet are spaced from each other when viewed in a direction perpendicular to the first surface of the substrate.

7. The transdermal administration device of claim 2, wherein the first and second adhesive sheets are formed such that an adhesiveness between the first and second adhesive sheets is lower than an adhesiveness of the first adhesive sheet to skin.

8. The transdermal administration device of claim 2, wherein the tear-off portion includes at least one starting portion formed in the flange.

9. The transdermal administration device of claim 8, wherein the at least one starting portion includes a plurality of starting portions formed in the flange.

10. The transdermal administration device of claim 9, wherein the remaining portion includes a plurality of remaining pieces formed along a periphery of the flange between the starting portions.

11. The transdermal administration device of claim 2, wherein the first and second adhesive sheets each have a circular outer shape.

12. The transdermal administration device of claim 11, wherein the weakened portion includes a surrounding portion and a starting point-forming portion, the surrounding portion is formed along a circle surrounding the main body when viewed in a direction perpendicular to the first surface of the substrate, and the surrounding portion has end points each connected to the starting point-forming portion which linearly extends from the surrounding portion to an outer edge of the flange.

13. The transdermal administration device of claim 1, wherein the remaining portion is part of the flange and positioned along an outer edge of the second adhesive sheet when viewed in a direction perpendicular to the first surface of the substrate.

14. The transdermal administration device of claim 13, wherein the first and second adhesive sheets are formed such that an adhesiveness between the first and second adhesive sheets is lower than an adhesiveness of the first adhesive sheet to skin.

15. The transdermal administration device of claim 1, wherein the remaining portion and the first adhesive sheet are spaced from each other when viewed in a direction perpendicular to the first surface of the substrate.

16. The transdermal administration device of claim 1, wherein the first and second adhesive sheets are formed such that an adhesiveness between the first and second adhesive sheets is lower than an adhesiveness of the first adhesive sheet to skin.

17. The transdermal administration device of claim 1, wherein the first adhesive sheet has an outer shape which is circular, oval or rectangular.

18. The transdermal administration device of claim 17, wherein the first and second adhesive sheets each have a circular outer shape.

19. The transdermal administration device of claim 1, wherein the second adhesive sheet has an outer shape which is circular, oval or rectangular.

20. The transdermal administration device of claim 1, wherein the tear-off assistance portion is a weakened portion having perforation and including a surrounding portion and a starting point-forming portion, and the surrounding portion has end points each connected to the starting point-forming portion which linearly extends from the surrounding portion to an outer edge of the flange.

* * * * *